(12) United States Patent
Godager

(10) Patent No.: US 11,385,084 B2
(45) Date of Patent: Jul. 12, 2022

(54) ELECTROMAGNETIC MULTIPHASE FLOWMETER

(71) Applicant: Wionetic AS, Sandefjord (NO)

(72) Inventor: Øivind Godager, Sandefjord (NO)

(73) Assignee: WIONETIC AS, Sandefjord (NO)

( * ) Notice: Subject to any disclaimer, the term of this patent is extended or adjusted under 35 U.S.C. 154(b) by 294 days.

(21) Appl. No.: 16/795,051

(22) Filed: Feb. 19, 2020

(65) Prior Publication Data
US 2020/0309580 A1 Oct. 1, 2020

(30) Foreign Application Priority Data

Mar. 29, 2019 (NO) .................................. 20190429

(51) Int. Cl.
| | | |
|---|---|---|
| *G01F 1/66* | (2022.01) | |
| *G01N 1/00* | (2006.01) | |
| *G01N 22/04* | (2006.01) | |
| *G01N 27/04* | (2006.01) | |
| *G01N 27/06* | (2006.01) | |
| *G01N 33/18* | (2006.01) | |

(Continued)

(52) U.S. Cl.
CPC .................. *G01F 1/66* (2013.01); *G01F 1/58* (2013.01); *G01N 22/00* (2013.01); *G01N 27/045* (2013.01);
(Continued)

(58) Field of Classification Search
CPC .... G01F 1/66; G01F 1/56; G01F 1/58; G01N 22/00; G01N 27/045; G01N 27/048;
(Continued)

(56) References Cited

U.S. PATENT DOCUMENTS

| | | | |
|---|---|---|---|
| 2,772,393 A | | 11/1956 | Davis |
| 4,429,273 A | * | 1/1984 | Mazzagatti .......... G01N 27/221 |
| | | | 324/676 |

(Continued)

FOREIGN PATENT DOCUMENTS

| | | |
|---|---|---|
| EP | 2 952 887 A1 | 12/2015 |
| GB | 2365978 A | 2/2002 |
| WO | WO 90/04167 A1 | 4/1990 |

OTHER PUBLICATIONS

Nash et al., "An Integrated Bidirectional Bridge with Dual RMS Detectors for RF Power and Return-Loss Measurement", Analog Dialogue 52-05, May 2018, p. 1-7.

(Continued)

*Primary Examiner* — David L Singer
*Assistant Examiner* — Fatemeh Esfandiari Nia
(74) *Attorney, Agent, or Firm* — Birch, Stewart, Kolasch & Birch, LLP

(57) ABSTRACT

An electromagnetic flowmeter and a method for measuring a property of a fluid composition are provided. The electromagnetic flowmeter includes a first electric conductor with first and second ends, arranged inside a fluid conduit carrying a fluid composition comprising hydrocarbons, an RF electric signal source, and a first dual signal detector including first and second input ports. The first terminal of the electric signal source is connected to the first end of the first electric conductor and arranged to induce an RF electromagnetic wave in the fluid conduit by supplying an input electric signal to the first end of the first electric conductor. The first and second ports of the signal detector are connected to the first and second ends of the first electric conductor, respectively.

13 Claims, 13 Drawing Sheets

(51) Int. Cl.
  *G01N 33/28* (2006.01)
  *G01N 22/00* (2006.01)
  *G01N 27/22* (2006.01)
  *G01F 1/58* (2006.01)
  *G01R 27/26* (2006.01)
  *G01N 27/08* (2006.01)

(52) U.S. Cl.
  CPC ........... *G01N 27/048* (2013.01); *G01N 27/06* (2013.01); *G01N 27/221* (2013.01); *G01N 33/1833* (2013.01); *G01N 33/2847* (2013.01); *G01N 27/08* (2013.01); *G01N 33/28* (2013.01); *G01R 27/2629* (2013.01)

(58) Field of Classification Search
  CPC .. G01N 27/06; G01N 27/221; G01N 33/1833; G01N 33/2847
  See application file for complete search history.

(56) References Cited

U.S. PATENT DOCUMENTS

| | | | |
|---|---|---|---|
| 4,590,431 A | 5/1986 | Anderson et al. | |
| 5,103,181 A * | 4/1992 | Gaisford | G01N 33/2823 324/645 |
| 5,168,240 A * | 12/1992 | Howe | G01N 27/221 340/603 |
| 5,341,100 A * | 8/1994 | Taylor | G01V 3/30 73/152.24 |
| 5,625,293 A | 4/1997 | Marrelli et al. | |
| 6,826,964 B2 | 12/2004 | Nyfors | |
| 8,076,950 B2 | 12/2011 | Wee | |
| 9,335,195 B2 | 5/2016 | Ong et al. | |
| 9,588,063 B2 | 3/2017 | Jakkula et al. | |
| 9,588,071 B2 | 3/2017 | Nyfors | |
| 2008/0319685 A1 | 12/2008 | Xie et al. | |
| 2013/0285677 A1 | 10/2013 | Hammer | |
| 2017/0248530 A1 | 8/2017 | Parker et al. | |
| 2018/0011033 A1 | 1/2018 | Karimi et al. | |
| 2018/0188211 A1 * | 7/2018 | Chiao | G01N 33/491 |
| 2018/0372523 A1 * | 12/2018 | Alkhabbaz | G01F 1/582 |
| 2021/0131843 A1 * | 5/2021 | Sulzer | G01F 1/588 |
| 2021/0270645 A1 * | 9/2021 | Ma | G01V 3/08 |

OTHER PUBLICATIONS

International Search Report for International Application No. PCT/NO2020/050043 dated Jun. 2, 2020.

* cited by examiner

ELECTROMAGNETIC MULTIPHASE FLOWMETER

TECHNICAL FIELD

The invention relates to instrumentation and measurement techniques to measure the flow quantity and water content in a produced fluid from an oil well. Moreover, it relates to managing the reservoir as well as the production, including the disposals of produced water.

BACKGROUND

The product of an oil and gas reservoir consists of a mixture of oil, gas and water. During production a natural mixture of the ingredients are produced. Thus, two- and three phase flows are often encountered upstream and the measurement of the phase- and flow rate is of particular importance for management. The complexity of oil-in-water flow structures creates a challenge to flow measurement.

The term water cut is used to indicate the ratio of water produced as a fraction of the total volume fluids or liquids passing through a pipeline.

The term water cut meter is used to describe a measurement device that measures the water cut.

Traditionally produced fluids and rates from an oil/gas well has been measured by separating the phases and measuring the separator outputs by conventional single-phase techniques. This is acceptable practice as long as the wells produce the same rate and ratio fluids with time.

However, as this is not the case, this practice establishes a poor control regime as it is time consuming to discover upstream production changes as well as to address them when producing from numerous wells to a common 3-phase separator unit. In real world, the production from candidate wells must then be shut and separately be directed to test separator or equivalent process apparatus to thoroughly measure the ratio and rate changes consequently. Thus, the upstream work to allocate a candidate well that contribute to abnormal production are time consuming, expensive and maintenance-intensive.

An alternative to replace time and maintenance intensive work, is to provide each well with metering equipment capable of identifying the fluid compositions and rates. Typically, such equipment would be Multiphase Flowmeters (MP-flowmeter) that are recognized by the industry and that yield good reservoir and production management as well as allocation means. However, such equipment is typically very volumetric, requires maintenance, and is cost intensive.

Over decades many researchers have developed different means and techniques of measuring multiphase flow. These involve Microwave (U.S. Pat. Nos. 6,826,964 and 5,625, 293), LC Impedance means (US2013/0285677), Radio-frequency resonance devices (U.S. Pat. No. 9,588,063), Nuclear magnetic resonance (U.S. Pat. No. 9,335,195), Electromagnetic resonating wave guide members to guide a field from a transmitting antenna to a receiving antenna (US 2017/0248530, and US 2018/0011033), Electromagnetic loss and phase measurements (U.S. Pat. Nos. 8,076,950, 9,588,071) to mention a selection of devices and methods.

In general, microwave energy provides a complex measurement and may include absorptive crude. However, once the absorption becomes too great (as in water continuous phase) the measurement degrades to a level where the resolution of the parameters measured are too small to be effective. LC or capacitance measurement technology are good for measuring in the range of 1 to 15 percent as long as the medium does not absorb much of the lower frequency energy. Some crude do and therefor the measurement becomes difficult. Both capacitance and microwave energy device require a homogenous fluid mixture which adds on to the complexity to measure in a petroleum fluid stream. Thus, typically they involve bulky mechanical mixers upstream to the measuring device that is exposed to wear and tear.

SHORT SUMMARY

A goal with the present invention is to overcome the problems of prior art, and to disclose a system and a method.

The invention solving the above mentioned problems is a multiphase flowmeter and a method for measuring a property of a fluid composition carried in a fluid conduit according to the independent claims.

An effect of embodiments of the invention, is that the amount of water in oil can be determined more accurately than with comparable water cut meters.

A further effect is that the flowmeter is simple to manufacture and use in real life situations, such as in process plants.

EMBODIMENTS OF THE INVENTION

In the following description, various examples and embodiments of the invention are set forth in order to provide the skilled person with a more thorough understanding of the invention. The specific details described in the context of the various embodiments and with reference to the attached drawings are not intended to be construed as limitations. Rather, the scope of the invention is defined in the appended claims.

The embodiments described below are numbered. In addition, dependent embodiments defined in relation to the numbered embodiments are described. Unless otherwise specified, any embodiment that can be combined with one or more numbered embodiments may also be combined directly with any of the dependent embodiments of the numbered embodiment(s) referred to.

An electromagnetic flowmeter, comprising;
  a first electric conductor with first and second ends, configured to be arranged inside a fluid conduit carrying a fluid composition comprising hydrocarbons,
  an electric signal source, and
  a first dual signal detector comprising first and second input ports, wherein a first terminal of the electric signal source is connected to the first end of the first electric conductor and configured to induce an electromagnetic wave in the fluid conduit by supplying an input electric signal the first end of the first electric conductor,
  the first and second ports of the signal detector are connected to the first and second ends of the first electric conductor, respectively.

According to the invention the signal from the signal source is a Radio Frequency (RF) signal. By connecting the RF source to an RF transmission line inside the fluid conduit, an RF electromagnetic wave is induced in the fluid conduit.

Further, the electromagnetic flowmeter may comprise any of the features listed below, independently or in combination:

The electromagnetic flowmeter may comprise a signal processor configured to receive signal parameter values representative of the transmission and/or reflection characteristics of the first electric conductor, and configured to determine a property of the fluid composition.

The first electric conductor may be a metal wire configured to be arranged as a spiral inside the fluid conduit. Insulating layers are added between the electric conductor and the tubular cell 14, as needed.

The electromagnetic flowmeter may comprise an insulating liner configured to be arranged between the inner wall of the fluid conduit and the first electric conductor.

The electromagnetic flowmeter may comprise a conductive layer 128a between the tubular cell inner wall and the electric conductor 13. Additional insulating layers are added between the tubular cell and the conductive layer and the conductive layer and the electric conductor, as needed.

The layers inside the tubular cell mentioned above, may be implemented as a sandwiched tubular liner assembly 27.

Figure 12B:
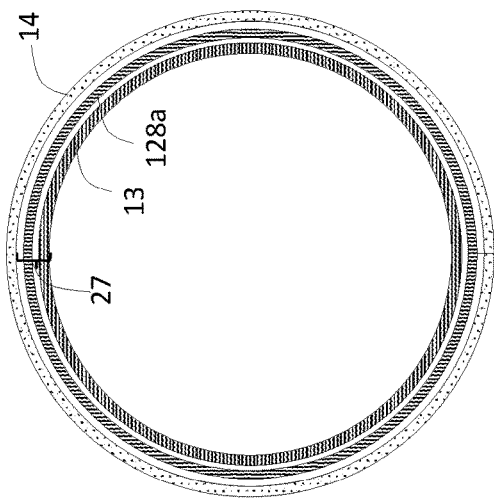
FIGS. 12a, 12b, 12c and 12d illustrate in sectional views, different embodiments of the invention.
Figure 12D:
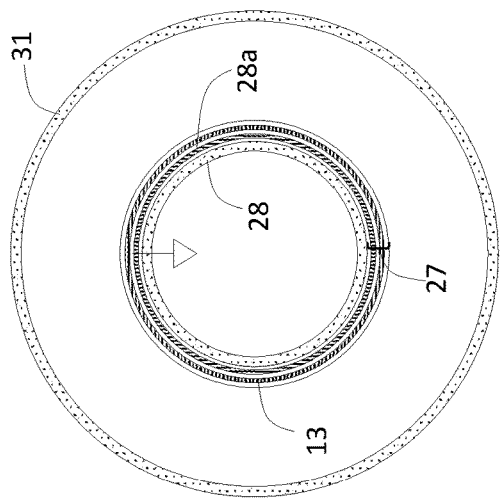
Figure 12A:
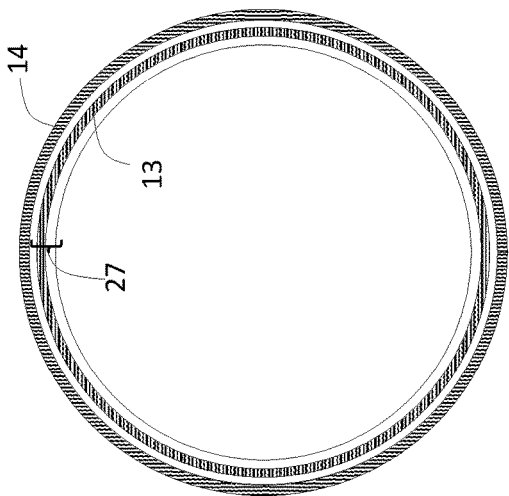

A protective layer may be provided inside the electric conductor in both cases illustrated in FIGS. 12a and 12b.

The first electric conductor may be embedded in the liner.

The fluid conduit may be electrically conductive and connected to an electric ground level.

A second terminal of the electric signal source may connected to the electric ground level.

The fluid conduit may comprise sealed through holes 25, 26 for the first and second ends of the first electric conductor.

In embodiments where a pipe is arranged inside the fluid connector, and fluid characteristics are measured in the annulus between the pipe and the fluid connector, the electromagnetic flowmeter may comprise; a grounded conducting layer 28a configured to be arranged around the inner tubular 28, where the electric conductor 13 is arranged outside the conductive layer 28a. Additional insulating layers are added between the inner tubular 28 and the grounded conductive layer 28a and between the grounded conducting layer 28a and the electric conductor, as needed.

The layers outside the inner tubular may be implemented as a sandwiched tubular liner assembly 27.

The electromagnetic flowmeter, may comprise the fluid conduit.

The electromagnetic flowmeter may be configured to provide a first measurement where the input electric signal has a first frequency, and a second measurement, where the input electric signal has a second frequency, wherein the first frequency is higher than the second frequency.

The processing unit may be configured to determine, based on the first and second measurements, respectively, a dielectric constant and a conductivity of the fluid composition.

The processing unit may be configured to determine any of a water content, an oil content, a gas content, a water-in-oil-ratio, an oil-in-water ratio, and a gas in oil ratio of the fluid composition based on the dielectric constant and the conductivity of the fluid composition.

The electromagnetic flowmeter may comprise network analyser, wherein the electric signal source and electric signal detector are comprised in the network analyser.

The processing unit may be configured to detect voltages and a phase difference of signals input on the first and second ports of the first electric conductor.

The first dual signal detector may comprise a bidirectional bridge with dual RMS and Peak-to-Peak detectors and a phase detector.

In an embodiment that may be combined with any of the embodiments above, the electromagnetic flowmeter comprises;
  a second electric conductor with first and second ends inside the fluid conduit, wherein the second electric conductor is arranged in line with the first electric conductor,
  a second dual signal detector 42, comprising first and second input ports, wherein
  the first and second ports of the second signal detector are connected to the first and second ends of the second electric conductor, respectively, and
  the processing unit is connected to the second signal detector and configured to determine a property of the fluid composition.

The processing unit may be configured to cross-correlate signals from the first and second detectors to determine any of a flow rate or flow direction of the fluid composition.

The first ends of the first and second electric conductors may be arranged adjacent each other, and the first terminal of the electric signal source is connected to the first end of the second electric conductor.

In an embodiment, the invention is a method for measuring a property of a fluid composition carried in a fluid conduit, comprising;

inducing an electromagnetic wave in the fluid conduit by supplying an input electric signal to a first end of a first electric conductor inside the fluid conduit, receiving an output electric signal from a second end of the first electric conductor, determining a property of the fluid composition based on the input electric signal and the output electric signal.

Further, the method may comprise any of the flowing features alone or in any combination;

determining the property in addition is based on a reflected input electric signal.

converting a synthesized wave in a digital-to-analog converter to obtain an analog sinusoidal waveform.

comparing amplitude and phase of any of the input electric signal, the output electric signal and the reflected input electric signal.

determining a propagation coefficient.

providing a first measurement where the input electric signal has a first frequency, and a second measurement, where the input electric signal has a second frequency, wherein the first frequency is higher than the second frequency.

determining, based on the first and second measurements, respectively, a dielectric constant and a conductivity of the fluid composition.

determining any of a water content, an oil content, a gas content, a water-in-oil-ratio, an oil-in-water ratio, and a gas in oil ratio of the fluid composition, based on the dielectric constant and the conductivity.

A detailed description of embodiments of the system is given in the following.

The water-cut flow meter and metering technique of this invention is intended to measure fluid properties of a flow process. It may, in an embodiment, based on a tubular segment that is part of the pipeline system feeding fluids from a well into a production header, see FIG. 2.

The tubular segment is provided with a conductive transmission line that is exposed to the process media flowing through it. An electrical signal is induced to one end of the transmission line and is guided along the line through a sample section (cell) having a stream of petroleum fluid passing through it.

As the EM wave propagates along the transmission line the wave speed and energy level guided will be affected by the dielectric constant and the conductivity of the fluid exposed. Consequently, there will be a change in energy level and phase of the wave as it propagates. In absolute terms, the amount of change will be depending upon the physical properties of the transmission line and how much water and oil there is in the sample section. However, as the properties of the transmission line will be known and the same (fixed/constant) the relative changes measured at the reception will be directly with respect to the fluid properties.

Further, a cell having a simple transmission line constructed in part by a metal wire has a very wide bandwidth. It is much wider than the bandwidths seen by prior art that utilize transmitting and receiving antennas, phase-lag or attenuation devices, or resonance measuring devices. The dielectric property of produced water is typically=80, oil=3, and natural gas=1, so any small change in water content will produce a rather large contrast in their electrical properties. According to theory, sampling at lower frequency will respond to resistivity or conductivity. Vise-versa, at higher frequency sampling will respond to the dielectric property changes of the media.

Measurement of the EM-wave propagation along a transmission line may be done from a medium range into a very high frequency domain. This in turn, eases the physical construction of an application specific apparatus. It provides dimensional and functional freedom to make an advanced flow instrument that would fit any size upstream petroleum requirement. Further, utilizing a simple transmission line enhances the science to obtain multi-parameter measurements in any process flow and size configuration, either the flow is inside or outside a tubular member.

Furthermore, if the transmission line is spiraled numerous of turns over a tubular section the propagation of the EM-wave will more represent a capture of the true fluid composition within the cell, thus, eliminating the need of a mechanical mixer. Moreover, the water-cut meter may be installed in either vertical or horizontal position.

A signal detector device monitors the propagation of the EM-wave and a signal processor digests the measures taken and outputs engineering values representing the oil-in-water or the water-in-oil contents respectively. The processor outputs are then transmitted to an indicator station monitoring and recording the water-cut of the petroleum stream in accordance with the received signals from the signal detector.

Figure 1:
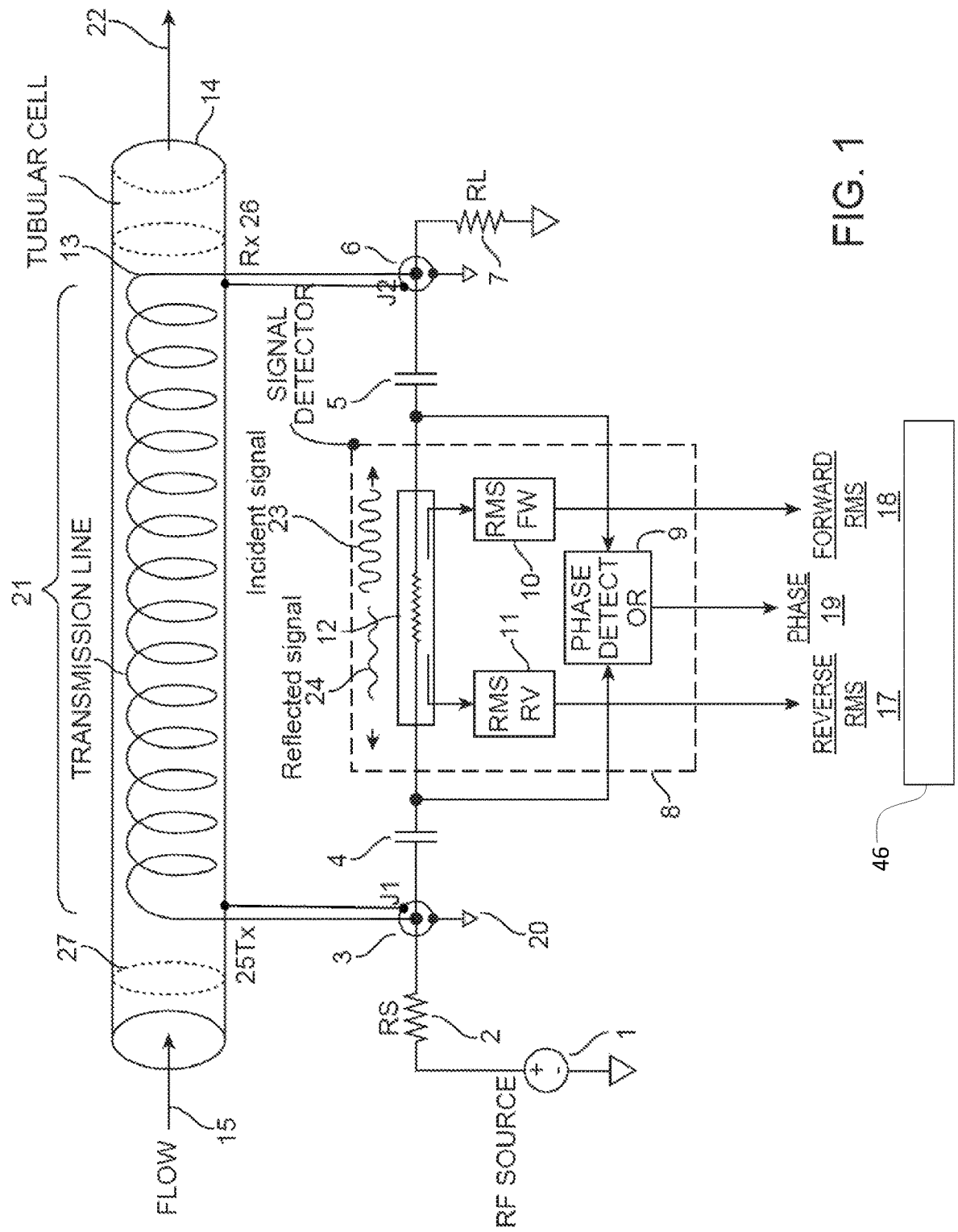
FIG. 1 is a schematic diagram illustrating a water-cut flowmeter (WCM) with spiraled electric conductor, signal source and detectors according to an embodiment of the invention.

By FIG. 1 we will teach an introductory description of the watercut meter of this invention and its advantages. Hereinafter, a more detailed description of the signal and transmission line performance will be given.

The water-cut meter shown in FIG. 1 includes an electric signal source, such as a Radio Frequency (RF) source or transmitter, 1 providing electromagnetic energy, hereafter called RF-source. The RF-source 1 is low power and operates from medium to very high frequency band (1 MHz-300 MHz) and may use a digital signal processing to synthesize a waveform followed by a digital to analog converter (DAC) to produce an analog sine wave output. The RF-source 1 provides RF-power to the transmission line 21 via serial impedance RS 2 and transmit junction J1 3. Transmission line 21 is a wave guide comprising an electric conductor, such as a wire 13 and ground 20.

The conductance of the RF-energy is carried out by the transmission line 21 as a wave-guide and is terminated at the receiver side J2 6 and by impedance match circuit RL 7. The tubular cell 14 has a flow input line 15 carrying a stream of multi-phase petroleum stream. The flowing stream 15 is leaving the tubular cell 14 in line 22. The tubular cell 14 will be described in further detail hereafter. The RF-signal injected to the transmission line wire 13 is guided along, and by the wire 13 and conductive ground 20, and as it propagates it is exposed to the petroleum stream passing from inlet line 15 to outlet line 22. Thus, as the RF-signal injected at J1 3 is guided along the transmission line 21, the energy is absorbed by the stream. By measuring the amplitude of the wave as it is injected at J1 3 and comparing it with the amplitude at the reception J2 6 the energy absorbed by the stream may be accomplished.

Signal detector 8 is a bidirectional bridge with dual RMS and Peak-to-Peak detectors, 10 and 11, for RF power and return-loss measurement in accomplishment with an phase detector 9. The latter, measuring the phase-lag between the incident 23 and the returned 24 signal at reference point J1 3 and J2 6 respectively.

The signal detector 8 in this application are coupled with capacitors 4 and 5 respectively to provide cut-off of any DC components to the incident 23 and return 24 input signal lines.

A directional coupler configuration comprising 10, 11, and 12 is used to sense RF power at 31 and 32 in the signal chain monitoring performance of the RF-signal as it propagates along the transmission line 21.

Furthermore, a second parameter is measured by signal detector 8, where a phase detector 9 compares the phase of the incident 23 and return 24 path signals. The difference between the phases, namely the phase lag will give additional information of the RF-signal propagation over the transmission line 21. Both the RMS/Peak-to-Peak outputs 17 and 18 as well as the phase output 19 are required to estimate the water-cut of the petroleum stream flowing. The relationship between the parameters 17, 18, and 19 measured by the signal detector 8 and the water-cut stream will be described later. The output from the signal detector may be s-parameters. S-parameters is a standard way of characterizing a high-frequency circuit, by determining the reflection and transmission characteristics in the frequency domain.

For those skilled in the art, the measurement set-up described above is often referred to as vector network analyzer type. The term "vector network analyzer measurement' means that:

both the magnitude and the phase is measured the s parameters are measured

Normally, the voltage or current at any point of the measurement section will have two terms. One forward wave and one reflected wave respectively, as described in equation 5, below. To measure the propagation constant k in equation 5, one needs to separate those two waves. E.g. measuring the forward wave means measuring s12 in s-Parameter.

Figure 2:
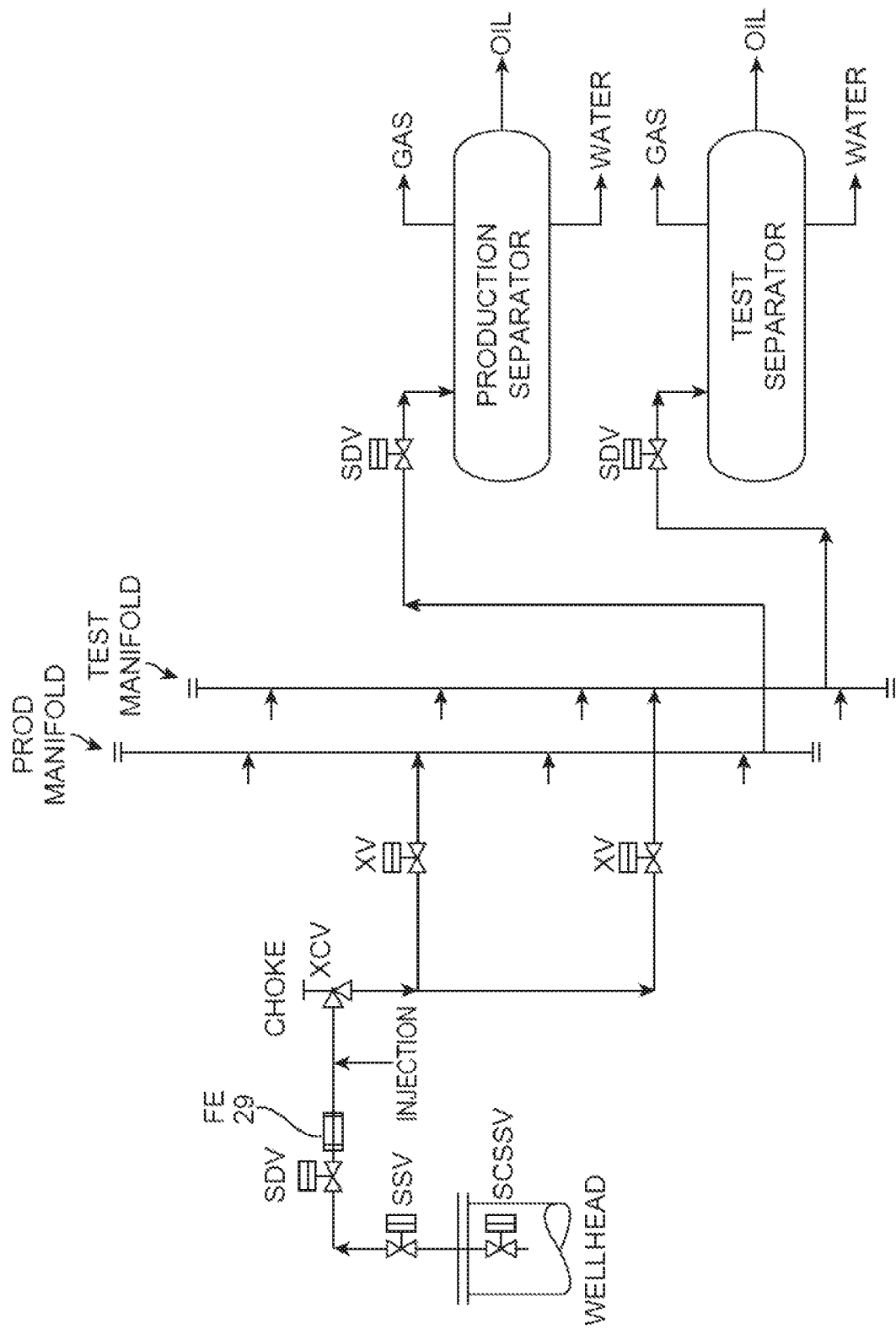
FIG. 2 shows schematically an overall process system from the well with flow-lines, the manifold headers for test and production respectively and a receiver 3-phase separator.

A typical application of this instrumentation is shown in FIG. 2, illustrating an apparatus 29, hereafter often referred to as a Flow Element (FE). The flow element 29 of this invention is to measure and monitor a process stream volumetric water-cut mixture in real time. As an EM wave propagates along a transmission line the wave speed and attenuation will be dependent on the dielectric constant and the conductivity of the surrounding process media (oil-water-gas mixture). Thus, by sampling the propagation of a guided EM-wave along a transmission line constructed by a wire and a metal ground, the water-cut of the process media may be monitored.

Figure 3:
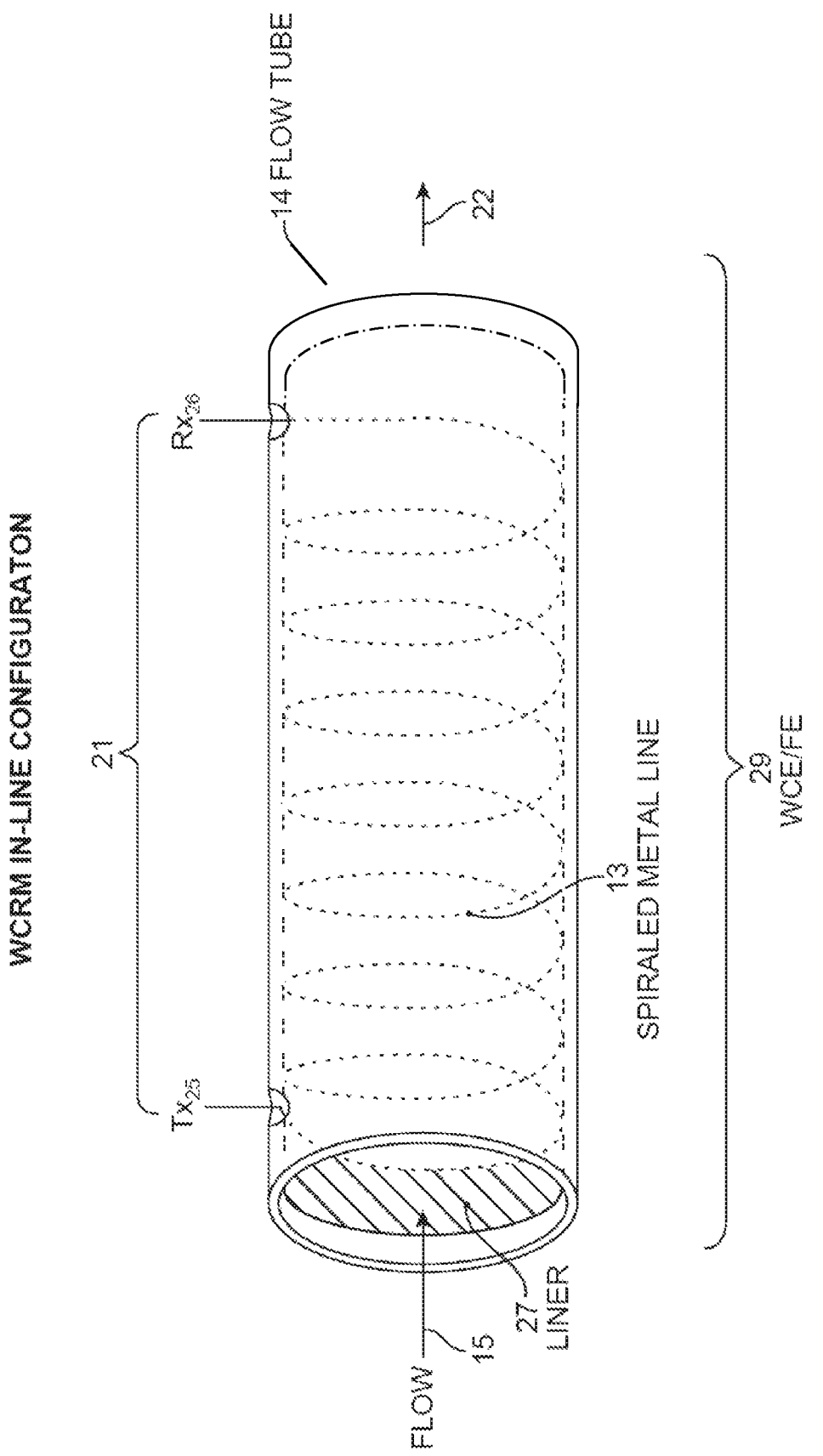
FIG. 3 shows an outline drawing of an inline embodiment of the WCM responding to a media flowing inside a tubular member.

With reference to FIG. 3 we illustrate the full assembly of an in-line configuration Water-Cut Element (WCE) 29, also in literature often referred as Flow Element (FE). Note that we use the expression in-line of this configuration as the flow element 29 is designated to measure the water-cut of an petroleum stream that flow coaxially inside and though the tubular cell 14 entering line 15 and outlet line 22.

Further, the illustration show the tubular cell 14 having RF entrance ports Tx 25 and Rx 26. Inside tubular cell 14 as represented with dashed lines are the liner 27 with a spiraled metal line 13 embedded. The liner 27 and embedded spiraled metal line 13 defines the cell waveguide or transmission line assembly 21 with its entrance and exit ports 25 and 26 respectively.

Also shown in FIG. 3 are fluid entrance line 15 and exit line 22.

In FIG. 3, and also illustrated in FIG. 12*a*, the tubular cell 14 is connected to the same ground as the signal source and the signal detector. The electric conductor 13 is arranged inside the inner wall of the tubular cell 14. Insulating layers are added between the electric conductor and the tubular cell 14, as needed.

In an alternative embodiment, illustrated in FIG. 12*b*, the electric conductor (13) is spun inside a conductive layer 128*a*. The conductive layer 128*a* is connected to the same ground as the signal source and the signal detector. Additional insulating layers are added between the tubular cell and the conductive layer and the conductive layer and the electric conductor, as needed.

The layers inside the tubular cell may be implemented as a sandwiched tubular liner assembly 27, as illustrated in FIGS. 12*a* and *b*, or as a combination of separate liners or segments. A complete liner assembly may be advantageous in certain situations, since it will constitute a complete, configured and resistant sensor element of the electromagnetic flowmeter that may be installed inside pipes where flow characteristics in the pipe should be measured.

A protective layer may be provided inside the electric conductor in both cases illustrated in FIGS. 12*a* and 12*b*.

Figure 4:
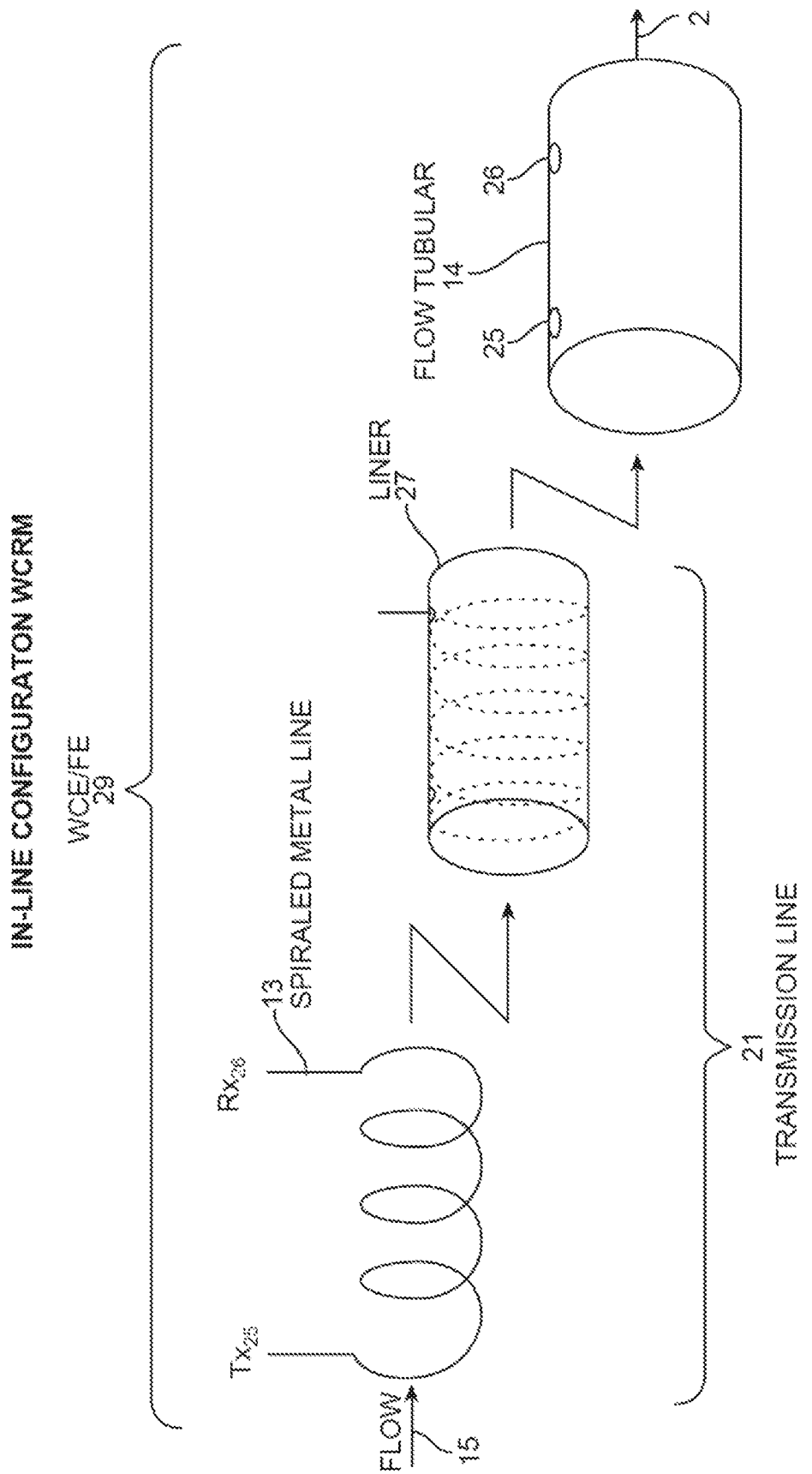
FIG. 4 Shows an expanded view of the in-line configuration of the WCM in FIG. 3.

FIG. 4 shows an expanded assembly drawing of the WCM. This shows the tubular cell 14, which typically is made out of a metal tubular segment. Liner 17 is made in an insulating material and has the transmission line 13 embedded. A preference embodiment 27 would have the transmission line 13 casted into it.

In an embedded application the transmission line 13 may be a metallic non-insulated wire as the liner material would provide the waveguide insulation. Vise-versa, in a non-embedded application the transmission line should be made using a metallic insulated wire. Viewing the flow element 29 as seen on FIG. 3 the petroleum stream are passing longitudinally through a channel that has no obstructions from inlet 15 and out through outlet 22. By means, the flow is not restricted by any obstacles within the flow element 29.

For those skilled in the art of flow measurement this is often referred to as a wetted but non-intrusive flow element, meaning the flow element 29 has embedded a transmission line assembly 21 that is in contact with the fluid (wetted) but it is not disturbing or obstructing the process stream.

Moreover, it should be noted that the transmission line assembly 21 is located in recess of the inner wall of the tubular 14 making flow element 29 what we may call full-bore. However, the full-bore configuration, is more a favorable feature or preference characteristics of an apparatus and is not necessary to the practice of this invention. The use of a spiraled metallic line 13 embedded or held in place by liner 27 enables cross sectional and longitudinal exposure of the transmission line 21 as it increases the contact surface to the fluid stream.

Recalling this briefly, monitoring the propagation of a RF-signal that is guided along the transmission line 21 will define measurements being representative method to establish a volumetric water-cut of a flowstream as the incident signal 23 is sensitive to the fluid permittivity and conductivity over the sample interval or section.

An oil-in-water or water-in-oil process flow rarely appear homogenous, this way the proposed configuration of the transmission line 21 will provide a very representative sample-volume that enhance the monitor of the true fluid mixture flowing through the pipeline at any time. This feature eliminates the need for a homogenous fluid sample and cancels the need to make use of mechanical mixers upstream the flow element 29 as well as need of a specific physical orientation of the flow element 29 when it is mounted and servicing to monitor the fluid mixture in a petroleum pipeline.

Figure 5:
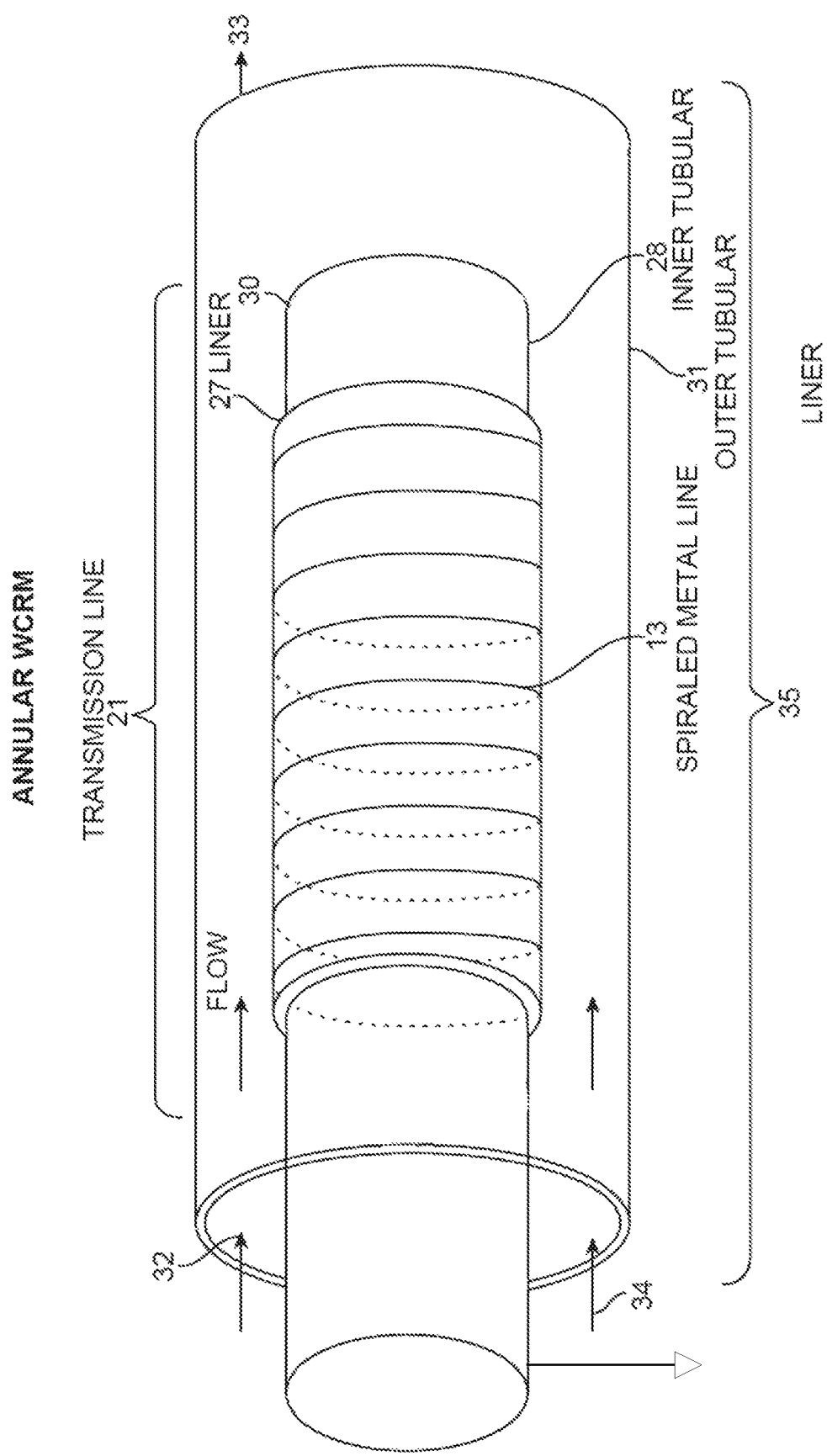
FIG. 5 shows the typical outlines of an annular embodiment of the WCM as responding to a media flowing in between an outer and an inner tubular member.
Figure 6:
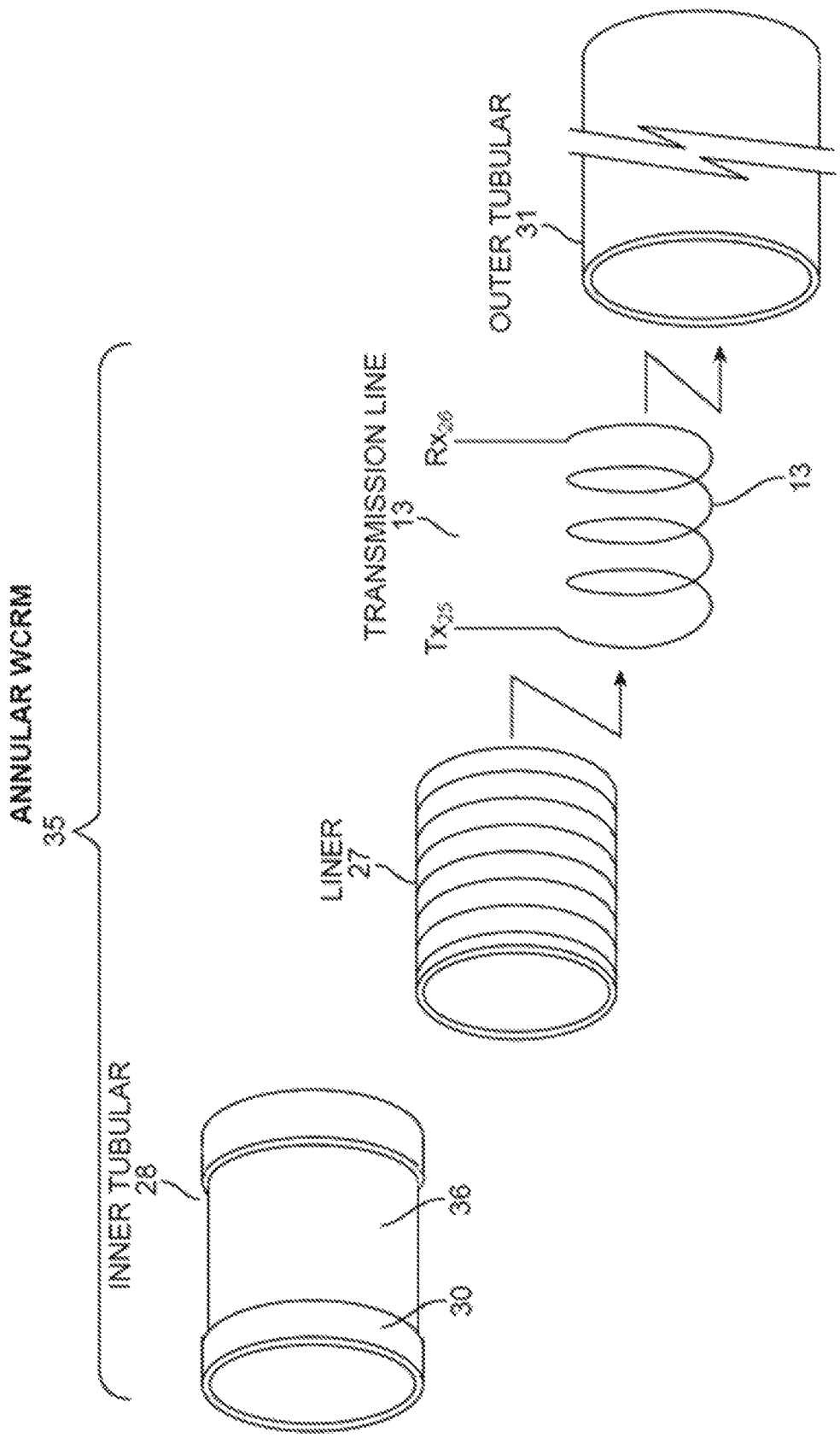
FIG. 6 is an expanded view of the annular embodiment of the WCM with its main components.

FIGS. 5 and 6 illustrates an alternative configuration of the WCE 35. Here the WCE 35 is attached to a tubular element 28, which is encapsulated of a second and outer tubular element 31. In turn the liner 27 and spiraled metal line 13 is attached and be part of the outside wall 30 of the tubular 28. In this configuration the transmission line 21 would be subject to measure fluid properties of an intermediate flowing process stream 34, which in literature often is referred to as an annular stream. The annular stream 34 having the flow input line 32 and an outlet line 33 respectively.

With exception of the different configuration the annular meter WCE 35 have the same characteristic liner 27, spiraled metal line 13, and the same option configuration of the latter two as described above for the in-line configuration meter 29. In FIG. 6 we see the liner 27 providing host for a spiraled metallic line 13 defining the transmission line 21 covering a cross sectional and longitudinal section of the annular space between inner tubular 28 and the outer tubular 31.

Further, the inner tubular 28 is provided with a recess 36 to embed the transmission line assembly 21. Again, the recess 36 and embedment for 21 is provided to avoid obstructions in the flow path and is more a favorable feature or preference characteristics of an apparatus and is not necessary to the practice of this invention. However, it makes the coaxial channel between the inner tubular 28 and the outer tubular 31 full-bore.

Recalling again, this configuration and measurement will provide a volumetric representation of the water-cut of an annular process stream. Again it is not sensitive to require a homogenous oil-in-water mixture fluid stream and the WCE 35 is neither sensitive to physical orientation, nor mounting.

Due to the longitudinal spiraled metal line 13 along the tubular axes, propagation of an incident RF-signal 25 will be highly exposed to the process stream and at all time reflect a very good measure of the volumetric water-cut mixture as the signal is highly sensitive to the permittivity and conductivity of the fluid.

Figure 12C:
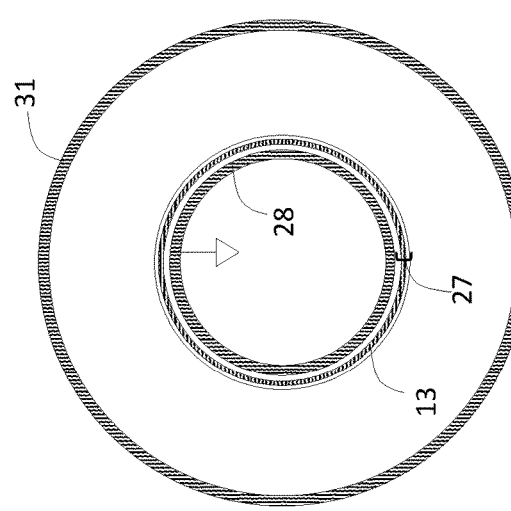

In FIG. 5, and also illustrated in FIG. 12c, the inner tubular 28 is connected to the same ground as the signal source and the signal detector. In this way the inner tubular with the liner and the electric conductor e.g. metal wire, will act as a complete floating sensor element that may be easily installed in wellbores to provide measurements in the annulus around the liner. Insulating material is provided between the liner and the electric conductor.

In an alternative embodiment, illustrated in FIG. 12d, a grounded conducting layer 28a may be added around the inner tubular 28. The electric conductor 13 is arranged outside the conductive layer 28a. Additional insulating layers are added between the inner tubular 28 and the grounded conductive layer 28a and between the grounded conducting layer 28a and the electric conductor, as needed.

The layers outside the inner tubular may be implemented as a sandwiched tubular liner assembly 27, as illustrated in FIGS. 12c and d, or as a combination of separate liners or segments. A complete liner assembly may be advantageous in certain situations, since it will constitute a complete, configured and resistant sensor element of the electromagnetic flowmeter that may be installed around pipes where flow characteristics of the annulus should be measured.

A protective layer may be provided outside the electric conductor and liner in both cases illustrated in FIGS. 12c and 12d.

Figure 7:
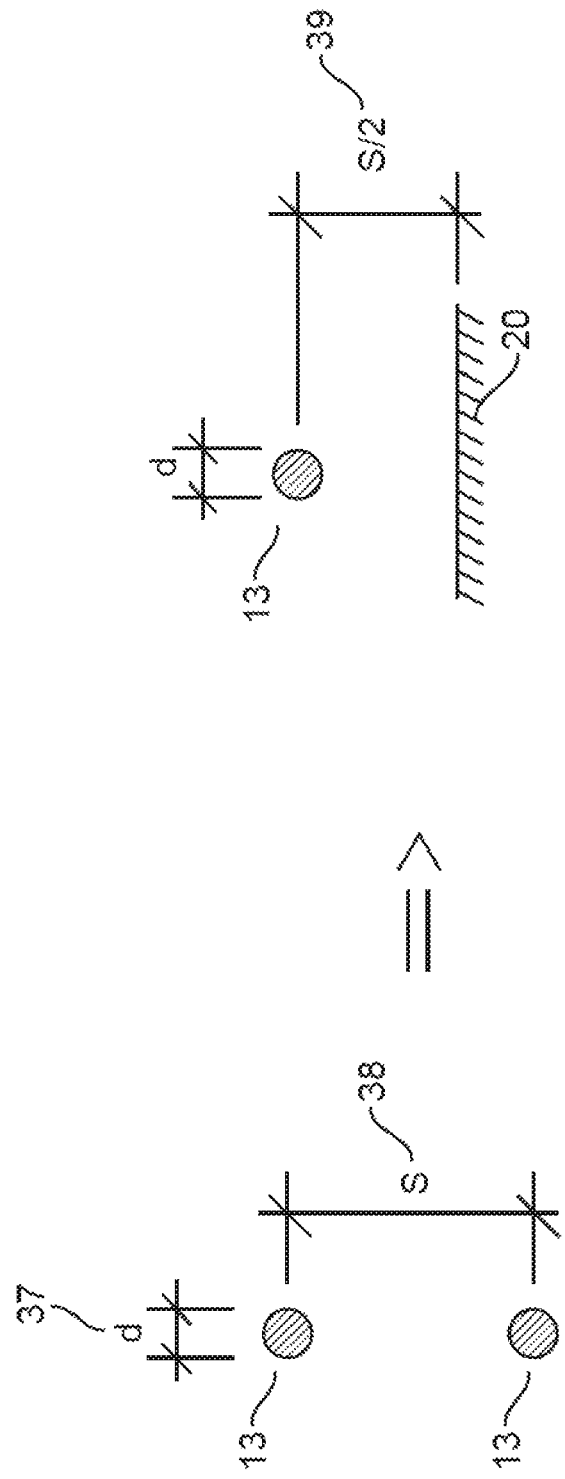
FIG. 7 illustrates the equivalence between a transmission line with parallel wires and a single spiral line and a ground plane.

Now referring to FIG. 7 to give a more detailed description of the propagation of the incident 23 and reflected 24 RF-signal on the transmission line 13.

We want to establish expressions for the Capacitance C, Inductance L, and Conductance G, for the spiral line 13. By introducing a ground metal plane 20, a parallel wires transmission line equivalent to a single wire 13 above the metal plane 20, see the equivalence derived in FIG. 7. The single wire 13 and ground plane structure 20 can be used to analyze a spiral line, as long as the distance between the spiral turns are much larger than the distance between the wire 13 and ground plane 20.

The capacitance and inductance of the parallel wires and the wave propagation along the wire 13:

$$\text{Capacitance } C, \left[\frac{\text{Farads}}{\text{meter}}\right] \quad C, \ = \frac{\pi \varepsilon_1}{\cosh^{-1}\left(\frac{s}{d}\right)} \qquad [1]$$

$$\text{External inductance } L, \left[\frac{\text{henry}}{\text{meter}}\right] \quad L, \ = \frac{\mu_1}{\pi}\cosh^{-1}\left(\frac{s}{d}\right) \qquad [2]$$

$$\text{Conductance } G, \left[\frac{\text{mhos}}{\text{meter}}\right] \quad G, \ = \frac{\pi \sigma_1}{\cosh^{-1}\left(\frac{s}{d}\right)} = \frac{\pi \omega \varepsilon_0 \varepsilon''}{\cosh^{-1}\left(\frac{s}{d}\right)} \qquad [3]$$

In expressions [1] and [2] above C and L are respectively capacitance and inductance per unit length of the parallel wires 13.

Where $\varepsilon_1$ is equivalent dielectric coefficient, and $$\varepsilon_1 = \varepsilon_r \varepsilon_0 - \frac{j\sigma}{\omega}, \qquad [4]$$

where
  $\varepsilon_r$ is relative dielectric coefficient
  $e_0$ is the dielectric constant of air
  $\sigma$ is the conductivity, and
  $\mu_1 = \mu_0$ is the magnetic permeability Thus, the wave propagating along transmission line 13 can be written as S-parameters based on the wave equations:

$$W(x) = \alpha e^{-jkx} + be^{jkx} \qquad [5],$$

where the first term $\alpha e^{-jkx}$ is the forward or incident wave 23 and $be^{jkx}$ is the reflected wave 24.

S11 is defined as the ratio of the reflected wave to the incident wave. Thus:

$$S11 = \frac{be^{jkx}}{ae^{-jkx}} = \frac{b}{a}e^{2jkx} \qquad [5a]$$

In equation [5] and [5a], k is the propagation coefficient, and:

$$k = 2\pi f\sqrt{LC} = 2\pi f\sqrt{\varepsilon_1 \mu_0} = \omega\sqrt{\varepsilon_1 \mu_0} \qquad [6]$$

Conclusively, the main task of the WCM 29 and 35 is to establish the propagation coefficient k in equation [6] which is expressed in complex means by dielectric coefficient $\varepsilon_1$, and $\varepsilon_1$ is further related to relative dielectric constant and conductivity of the mixed fluid stream by using equation [4].

Hence, the main objective to measure the water-to-oil or oil-to-water composition of the petroleum fluid stream is to measure the wave along the transmission line 21 as shown in equation [5], find the S-parameters, e.g. S11, and to obtain the propagation coefficient k. Then in turn, from the propagation coefficient k to find the relative dielectric constant and conductivity, and then resolve to obtain the ration of water-to-oil of vise-versa.

Then to summarize, the advantages using a transmission line is that it is a wide bandwidth device, which enables the multiple frequency measurements.

The impedance of the transmission line is:

$$Z_0 = \sqrt{\frac{L}{c}} = \frac{120}{\sqrt{\varepsilon_1}} \cosh^{-1}\left(\frac{s}{d}\right) \qquad [7]$$

Where $\varepsilon_1$, s and d are defined before.

In eqn [7], only $\varepsilon_1$, defined in eqn [4], is frequency dependent. When using high frequency, $\varepsilon_1$ is no longer frequency dependent.

Eqn [7] can be used to determine the ratio of the line distance s to the diameter of the wire, when the impedance $Z_0$ is chosen.

Furthermore, the use of multiple frequency measurement will yield the additional advantages:

First, according to eqn [4], one can see that when using higher frequency, the dielectric term dominates. While using low frequency, the conductivity term dominates. The use of multiple frequency measurement makes it possible to measure both the dielectric and conductivity property of the fluid.

Figure 8:
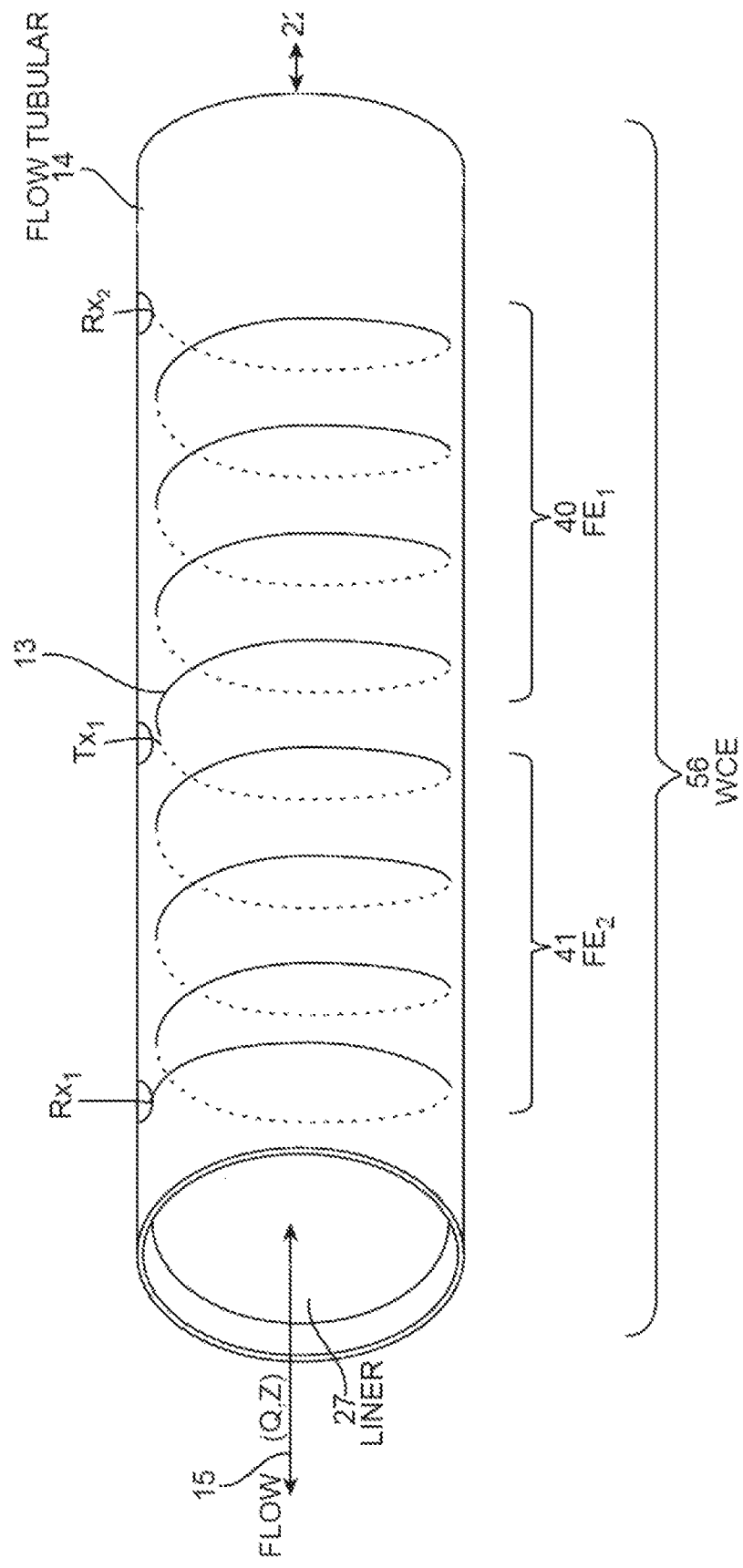
FIG. 8 illustrates in an embodiment a multivariate WCM having a split transmission line configuration to incorporate the measurement of the speed and direction of the flow-stream in addition to the water-cut.
Figure 9:
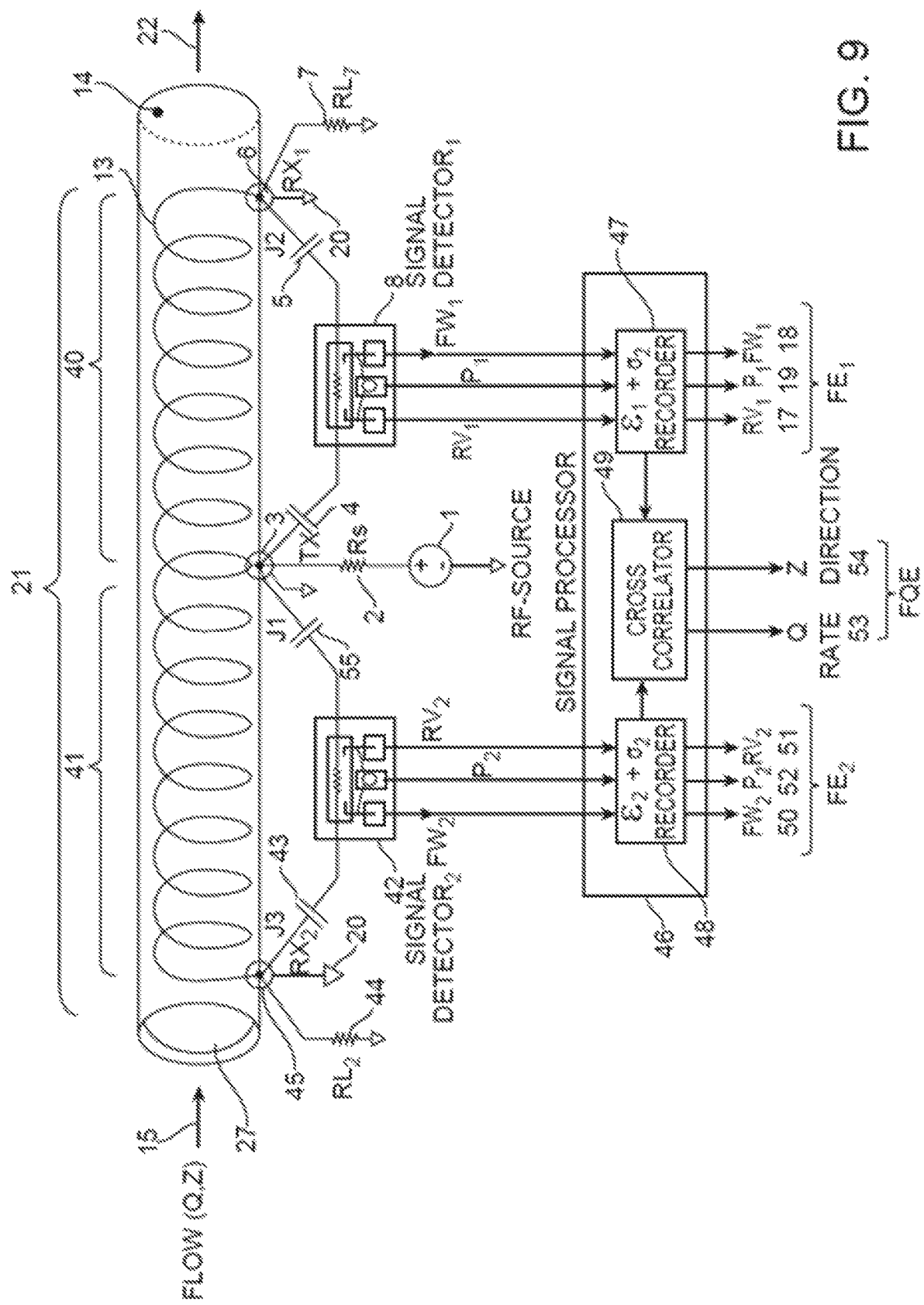
FIG. 9 shows the schematically diagram of a multivariate water-cut flowmeter according to an embodiment of the invention, with split and spiraled transmission line, signal source and detectors

Secondly, the use of multiple frequencies makes it possible to measure the fluid travel speed using a split transmission line as shown in FIGS. 8 and 9.

Then, now referring to the use of spiraled transmission line and its advantages:

First, a spiraled transmission line measures the average material electrical properties around a circle, as described herein. However, there is a need to establish a few parameters as there is an accuracy limit for the measurement of the phase difference over the line. Assume the phase accuracy limit is for example 1 degree. Then we may say the total traveling phase should be the accuracy limit multiplied with a factor. For example we choose this factor as 10. That is to say we need a length L transmission line along which the phase of the wave will change 10 degrees.

We know that when traveling one wavelength, the phase changes with 360 degrees. Hence we have the following relations:

$$l > \frac{\lambda}{36} \qquad [8]$$

$$\lambda = \frac{2\pi}{k} = \frac{1}{f\sqrt{\varepsilon_1 \mu_0}} \qquad [9]$$

Where $\varepsilon_1$ is the equivalent complex dielectric constant in eqn 4, and f is the frequency.

The above two equations can be used to calculate the length of the spiral line. The turns of the spiral line is the length divided by $\pi d$ (d: diameter of the spiral). One can see that the lower the frequency used, the more the turns of the line need to be.

When only high frequency is used, only one turn spiral line may satisfy eqn [8]. The electric conductor may in an embodiment be a single turn spiral line.

Velocity factor and electric length are two terms that are related to the characteristics of a transmission line.

The velocity factor is the ratio of the speed of a wavefront in a medium, to the speed of light in a vacuum.

Figure 13B:
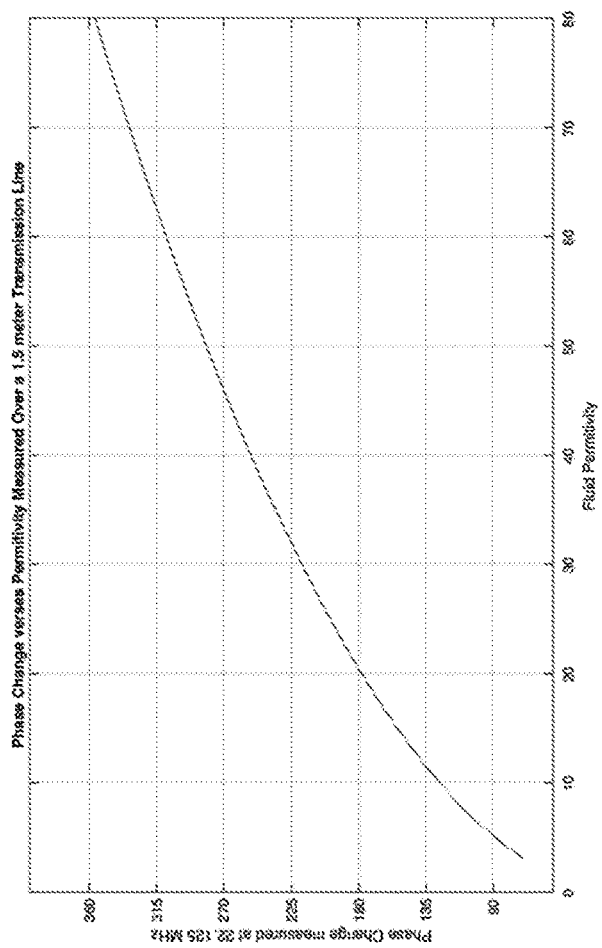
FIG. 13b illustrates the relationship between phase change and relative permittivity of the fluid for a transmission line of 1.5 m at a frequency of 22.125 MHz.
Figure 13A:
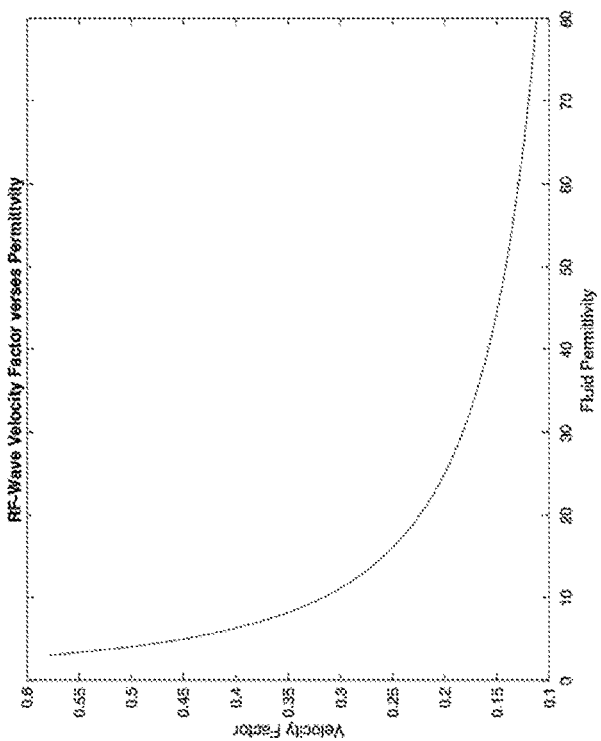
FIG. 13a shows an example of the relationship between the velocity factor and the relative permittivity of a fluid for a given frequency.

In FIG. 13a, an example of the relationship between the velocity factor and the relative permittivity of a fluid is illustrated for a specific frequency. These characteristics are often referred to in the terms of phase shift or "electrical length" at a given frequency. The "electrical length" is used to define phase shift introduced by transmission of an RF-Wave over a conductor or transmission line.

Due to the velocity factor of a particular transmission line, for instance, the transit time of a RF signal in a certain length of cable is equal to the transit time over a longer distance when traveling at the speed of light. So, for example, a pulse sent down a 2 meter long coaxial cable (whose velocity factor is 67%) would arrive at the end of the cable at the same time that the pulse arrives at the end of a bare wire of length 3 meters (over which it propagates at the speed of light), and one might refer the 2 meter section of coax having an electrical length of 3 meters. If the coax is loaded additionally the velocity factor would change correspondingly. So, for a 50° % factor the electrical length of the line would equal 4 meters. Thus, we see that the propagation of the RF-Wave is delayed in the transmission line and highly depending on the line electrical characteristics. Some transmission lines consist only of bare conductors, in which case their signals propagate at the speed of light, c. More often the signal travels at a reduced velocity κc, where κ (kappa) is the velocity factor, a number less than 1, representing a ratio of the speed of light.

Thus, in a transmission line, a signal travels at a rate controlled by the effective capacitance and inductance.

In the multiphase flow meter of the invention, the transmission line 13 and ground plane 20 are exposed to a dielectric fluid 34 filling the space in between the conductor 13 and ground plane 20. Thus, the relative permittivity or dielectric constant of the fluid effects the distributed capacitance along the transmission line 13. In turn, this reduces the velocity factor below unity. The velocity factor will also be reduced due to relative permeability $\mu_r$ of the materials surrounding the conductor 13 and the ground plane 20 which increase the disturbed inductance.

Taking permittivity and permeability properties of the cell into account as fluid flows through the Multiphase flow meter, the space between the transmission line 13 and the ground plane 20 is filled with a dielectric fluid of relative permittivity $\epsilon_r$. The velocity of the electromagnetic RF-wave is then reduced by the velocity factor κ stipulated below:

$$\kappa = \frac{v_p}{c} = \frac{1}{\sqrt{\epsilon_r \mu_r}} \approx \frac{1}{\sqrt{\epsilon_r}}. \qquad [10]$$

Thus, this reduced velocity factor would apply to propagation of the RF-signal along the transmission line which is immersed in a large space filled with that fluid dielectric. Part of the electromagnetic RF-wave surrounding each of the conductors feels the effect of the dielectric fluid, and parts are in free property space of multiphase flow meter. Then it is possible to define an effective relative permittivity $\epsilon_{eff}$ which then predicts the velocity factor according to:

$$\kappa = \frac{1}{\sqrt{\epsilon_{eff}}} \qquad [11]$$

$\epsilon_{eff}$ is computed as a weighted average of the relative permittivity of free space and that of the dielectric properties of the fluids as given in e.g. Table 1 below:

$$\epsilon_{eff} = (1-F) + F\epsilon_r \qquad [12]$$

where the Cell factor, F, expresses the effective proportion of space so affected by the dielectric fluid.

In the case of a space where the majority of the volume in between the transmission line 13 and the ground plane 20 is filled with a dielectric fluid, the Cell factor is unity, since the electromagnetic RF-wave is confined to that region. In some applications, typically as in smaller dimensions flow meters, the Cell factor can be much smaller due to dimensional proportions between the meters housing and the transmission lines. Regardless, any dimensional proportions mentioned, radio frequencies will have its velocity factor (as well as its characteristic impedance) specific for the application intended. In the case of an ideal flow meter, where the Cell factor F=1, the velocity factor is solely determined by the dielectric fluid properties according to e.g. Table 1 below.

For example, a typical velocity factor for a flow meter is 0.577, corresponding to a dielectric constant of 3.0 (typical for oil). Suppose we wish to send a 22.125 MHz signal down a short section of such a cable, and delay it by 36°. In free space, this frequency corresponds to a wavelength of $\lambda_0$=13.56 m, so a delay of $\lambda/10$ would require an electrical length of 1.36 m. Applying the velocity factor of 0.577, this results in a physical length of cable 0.78 m long.

Vice-versa, for a dielectric fluid corresponding to 80 (seawater) velocity factor is 0.112. Again, using the 22.125 MHz signal the resulting physical length of the cable would be reduced to 0.15 m to measure the same 36 degrees phase change.

Never the less, as the transmission line length of the WCM is given by the ratio of phase change needed to accurately measure the properties of the fluid is given by the lower dielectric values to be measured using a 22.125 MHz RF-Wave, the transmission line length would in typical application be 1.5 meter long.

As an example, the phase change measured to establish the fluid dielectric properties could typically be as illustrated in FIG. 13b, illustrating the relationship between phase change and relative permittivity of the fluid for a transmission line of 1.5 m at a frequency of 22.125 MHz. If we consider the endpoints of the graph, a phase difference of 69 degrees corresponds to a relative fluid permittivity of 3.0, while a phase difference of 360 degrees corresponds to a relative permittivity of 80.0.

Figure 13C:
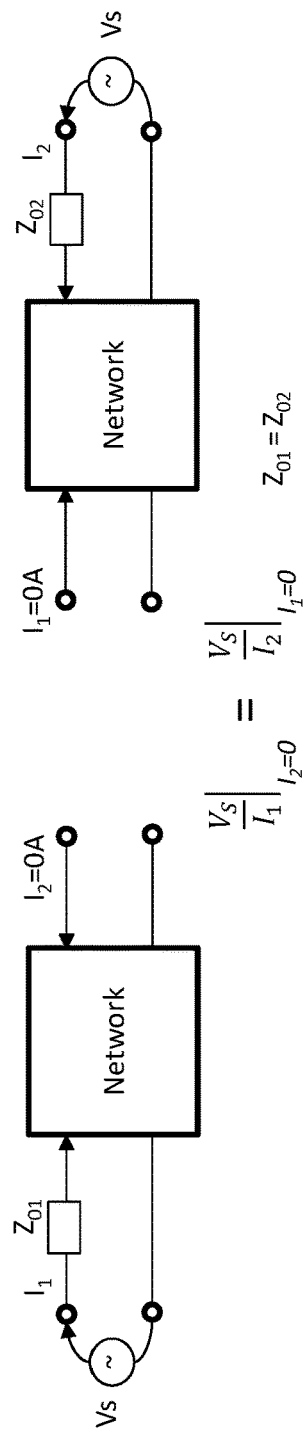
FIG. 13c illustrates the electrical properties of a symmetrical two port network.

The Multiphase flow meter of the invention is in an embodiment considered to be reciprocal or symmetric. The definition of symmetry is achieved if the electrical network properties of the cell are the same with reference to the input output ports. The cell may be represented by two-port network as shown in FIG. 13c.

The two-port network has an input and an output end, here marked $V_1$ and $V_2$ respectively and the network is said to be symmetrical if the ratio of excitation voltage to response current remains the same at both of the ports independently. This is shown in FIG. 13c where the Voltage to Current ratio for the both ports are equal. Thus, the network impedance expressed in Z-parameters, $Z_{11}$ and $Z_{22}$, are the same. In practice this describes the case of the multiphase flow meter 29 of FIG. 3. Here either side of the cell may be defined as input or output port due to the nature of the transmission-line 13 which provides the simplicity of a bare conductor in a housing. Moreover, either side may be used as input port for the fluid flow.

Further, the S- and Z parameters are interrelated, and S parameters can be found from Z parameters and vice-versa. For instance, the S parameter S11 for a two-port symmetrical network may be derived from the following Z-parameters:

$$S_{11} = \frac{(Z_{11} - Z_0)(Z_{22} + Z_0) - Z_{12}Z_{21}}{(Z_{11} + Z_0)(Z_{22} + Z_0) - Z_{12}Z_{21}} \quad [13]$$

Here the input impedance is the same on both sides of the network. I.e. $Z_0 = Z_{01} = Z_{02}$, as illustrated in FIG. 13c. Equation [13] may be further simplified taking into account that $Z_{11} = Z_{22}$, which is a condition for symmetry.

The other S-parameters can be derived from the Z parameters in the same way, as will be understood by a person skilled in the art.

In FIG. 8 we show an extended version water-cut meter configuration 56. The drawing illustrates a water-cut meter 56 having a split transmission line 13. This is an alternative embodiment of the invention that provides monitoring of flow rate (Q) and direction (Z) in addition the water-in-oil composition. The additional information is based on bivariate variables measured between the split legs 40 and 41 of transmission line 13. Again, in this embodiment the transmission line 13 is a spiraled metal line embedded or held in place by a liner assembly 27 and located internal tubular section 14 and the multiphase flowstream passes through the internal channel in either direction of this embodiment. Thus, the flow passage service as a bi-directional flow channel, having no specifically dedicated inlet/outlet ports 15 and 22 respectively.

Now referring to FIG. 9. The water-cut meter shown here includes a Radio Frequency (RF) source or transmitter 1, providing electromagnetic energy to the transmission line. The RF-source 1 is low power and operates from medium to very high frequency band (1-300 MHz) and may use a digital signal processing to synthesize a waveform followed by a digital to analog converter (DAC) to produce an analog sine wave output. The RF-source 1 provides RF-power to the transmission line 21 via serial impedance RS 2 and transmit junction J1 3. As seen form FIG. 9 the transmission line 21 in this configuration is split from a center junction 31 into two sections, section 40 and 41 respectively.

In both directions each of the metallic lines serves as a wave guide constructed by a wire 13 and ground 20. Again, the conductance of the RF-energy is carried out in both directions on respective waveguides and each line 40 and 41 is terminated at the receiver side J2 6 respective J3 45 and by impedance match circuits RL1 7 respective RL2 44.

The RF-signal injected to the transmission line wire section 40 and 41 is guided along the wire 13 and metal ground 20. As it propagates along the lines it is exposed to the petroleum stream passing from inlet/outlet line 15 to outlet/inlet line 22. The RF-signal injected at J1 3 and is guided along each of the line legs 40 and 41.

As the wave propagates along the spiraled line, energy is absorbed by the stream both directions. Thus, by measuring the amplitude of the injected wave as it appears at J1 3 and comparing it with the amplitude at the reception J2 6 and J3 45, in respective direction, the energy absorbed by the stream may be determined.

Signal detector 8 and 42 are both bidirectional bridges providing RMS, Peak-to-Peak, and phase measurements of the RF incident power and return-loss. The bivariate signal detector 8 and 42 in this embodiment are coupled with coupling capacitors 4, 5, 43, and 55 to provide cut-off of any DC components from the source and lines. Outputs of the signal detectors 8 and 42 are applied to a signal processor 46.

The signal processor performs mainly three tasks and operates in real-time. Real-time meaning the processor digests the signal at least 10 times faster than a parameter may change significantly.

First and second task is it provides signal filtering, image capture, and conversions of the outputs of the two signal detectors to establish the dielectric coefficient and conductivity of the fluidstream. This is performed by enhanced function blocks 47 and 48. Finally, the captured measurements of the flow are recorded to memory in respect to time for final task processing.

Third processing task is performed by flow-image processing by function block 49. For those skilled in the art will recognize the fact that by applying cross correlation of images captured and recorded in time domain by post processors 47 and 48, we will be able to create a captive picture of the flowstream.

Further they will know that the multiphase flowstream will not be smooth and entirely homogenous. Hence, the flowing liquid flowing through the water-cut meter 56 will contain dips and fringes measured at particular instants. As the fluid is moving, the fringes will move with. Thus, by using the cross correlator to capture and time-stamp as an event arise. Then in turn, lock on and observe as the event pass though the meter and be captured by downstream post processor.

As the downstream event image is captured the cross correlator may establish the time difference between the events. The time difference is directly related to the speed of the fluid stream as the distance between the transmission line section 40 and 41 is known. In turn, the flow rate quantity may be calculated when using the cross section area of the tubular 14. Furthermore, using the two post processors to capture the event images the direction of the flow stream may also me established.

FIGS. 8 and 9 refer to transmission line 21 as a singular continues and spiraled metal line with a balanced center tap 31 midway between the end terminals 32 and 33 respectively. It is to be expressly understood, however, that FIGS. 8 and 9 are for illustration only and are not to be construed as defining the limits of this embodiment of the invention. In this configuration the transmission lines may be constructed split into two or more separate and equal spiraled metallic lines and interconnected respectively to obtain the same service as prescribed herein.

As will be recognized by those skilled in the art, the innovative concepts described in this application can be modified and varied over a wide range of applications. By FIG. 10 we illustrate that the invention may embrace modifications and variations that include alternative sensor devices. One of ordinary skill in the art, with the benefit of this disclosure, will recognize the appropriate use of the methods and systems for a chosen application of a given or dynamic set of operating parameters given in FIG. 10, including pressure, temperature, flow rate, fluid composition, flow direction as well as salinity and/or conductivity of the aqueous phase, or various combinations thereof. Furthermore, the instrument and setup are constructed so that it may be integral part or device of any type industry standard for instrumentation. For this application a traditional 4-20 mA instrument loop configuration including a HART standard helps the instrument to digitally communicate with a receiver or monitor station over the same set of twisted-wires used to convey a traditional 4-20 mA analog instrument signal.

Moreover, including the HART standard and protocol will make present invention operate as a SMART transmitter compared to analog transmitters having a microprocessor as an integral part, which helps for self diagnostic abilities, non-linear compensations, re-ranging without performing calibrations, and ability to communicate digitally over the network.

Optionally, the methods and configurations of the present invention can be configured or combined in various schemes. The combination or configuration depends partially on the required precision and accuracy and the operational envelope of the process. One of ordinary skill in the art, with the benefit of this disclosure, will recognize the appropriate combination of configuration for a given application.

Figure 10:
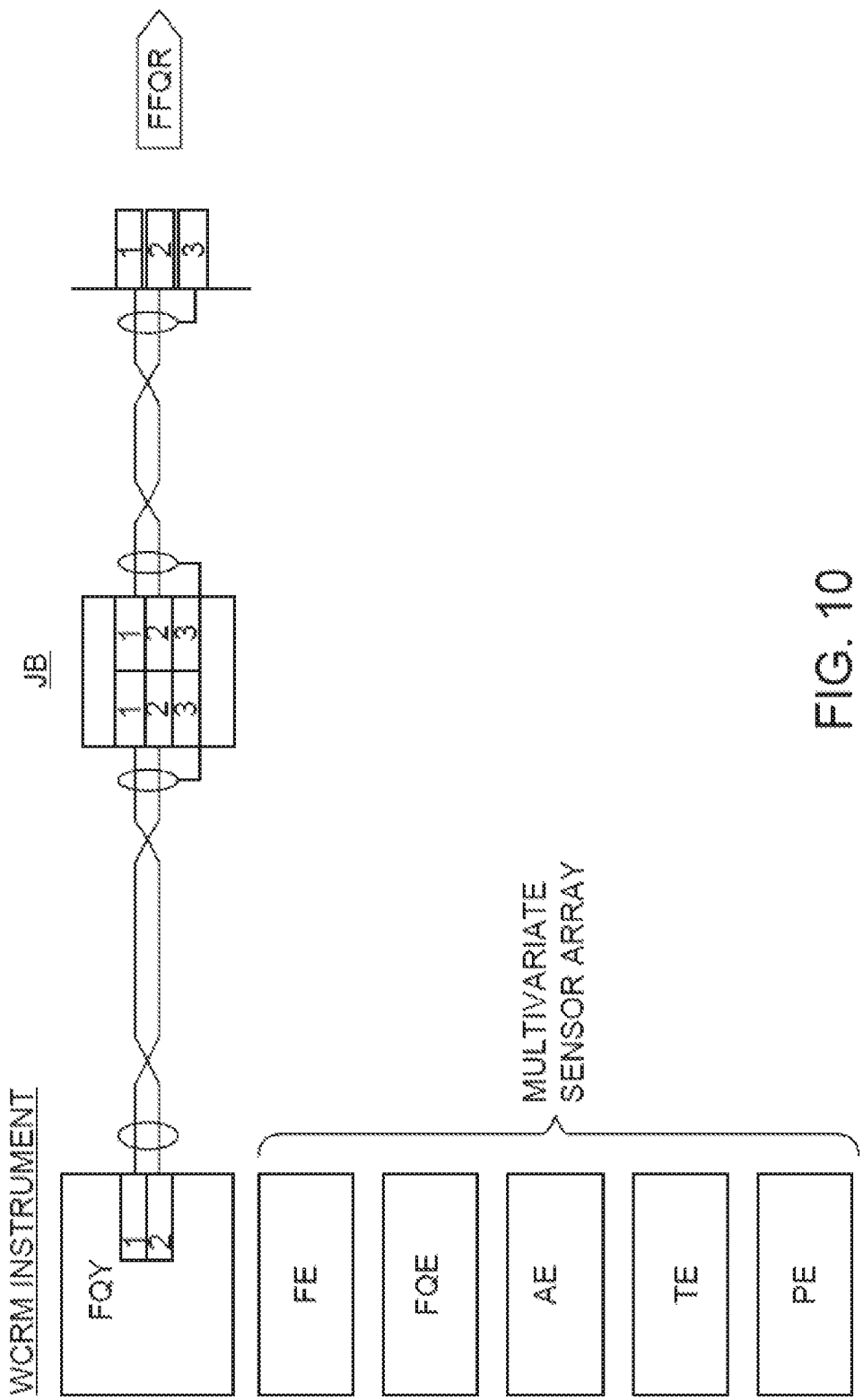
FIG. 10 shows an embodiment of the instrument block diagram of the WCM and its sensor configuration.
Figure 11:
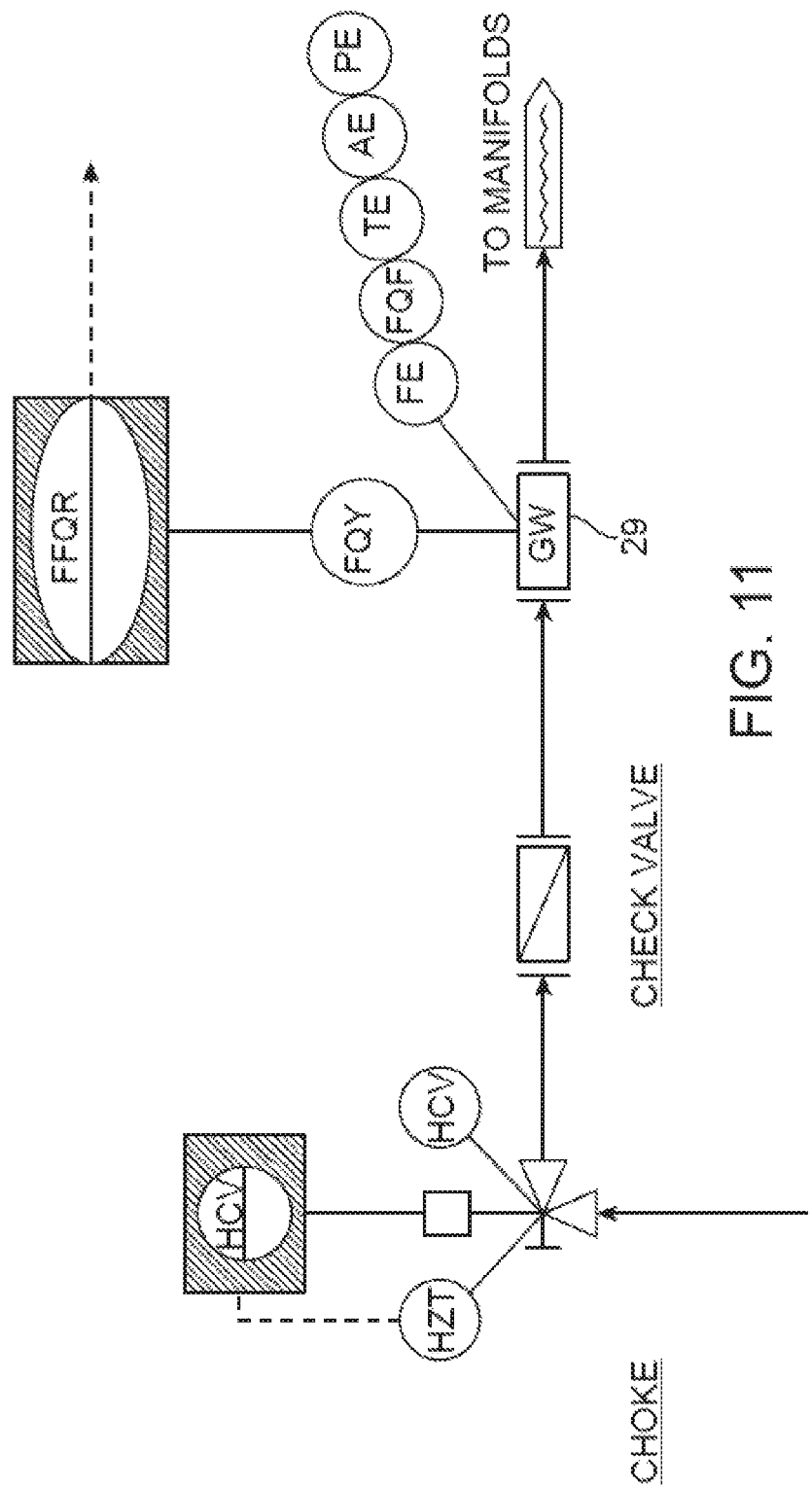
FIG. 11 shows in an example a typical instrument loop diagram including the WCM connected to a typical process control system.

The configurations as shown in FIGS. 10 and 11 shows a setup that are typically used to measure the process flow rate and to estimate the water phase fraction and oil phase fraction in a multiphase petroleum stream. None of the description in the present application should be read as implying that any particular element, step, or function is an essential element which must be included in the claim scope. The scope of patented subject matter is defined only by the allowed claims.

TABLE 1, below, shows the characteristic dielectric and conductive properties of fluids produced from a well.

TABLE 1

| Typical electric properties of fluids produced from an oil well. | | |
|---|---|---|
| Petroleum Stream | Dielectric Constant | Conductivity S/m |
| Water | 80 | 3 |
| Oil | 3 | 0.01 |
| Gas | 1 | |

In the exemplary embodiments, various features and details are shown in combination. The fact that several features are described with respect to a particular example should not be construed as implying that those features by necessity have to be included together in all embodiments of the invention. Conversely, features that are described with reference to different embodiments should not be construed as mutually exclusive. As those with skill in the art will readily understand, embodiments that incorporate any subset of features described herein and that are not expressly interdependent have been contemplated by the inventor and are part of the intended disclosure. However, explicit description of all such embodiments would not contribute to the understanding of the principles of the invention, and consequently some permutations of features have been omitted for the sake of simplicity or brevity.

The invention claimed is:
1. An in-line electromagnetic flowmeter, comprising:
a transmission line comprising a first electric conductor with first and second ends, configured to be arranged inside a fluid conduit carrying a fluid composition comprising hydrocarbons;
a Radio Frequency electric signal source; and
a first dual Radio Frequency signal detector comprising first and second input ports,
wherein a first terminal of the electric signal source is connected to the first end of the first electric conductor and is configured to induce a Radio Frequency electromagnetic wave in the fluid conduit by supplying an input electric signal to the first end of the first electric conductor,
wherein the first and second ports of the signal detector are connected to the first and second ends of the first electric conductor, respectively, wherein the electromagnetic flowmeter comprises a signal processor configured to receive signal parameter values representative of the transmission and/or reflection characteristics of the first electric conductor, and configured to determine a property of the fluid composition, and wherein the first electric conductor is a metal wire configured to be arranged as a spiral inside the fluid conduit, and the electromagnetic flowmeter further comprises an insulating liner embedding the spiral metal wire.

2. The electromagnetic flowmeter of claim 1, wherein the fluid conduit or the insulating liner is connected to an electric ground level, similar to an electric ground level of the electric signal source.

3. The electromagnetic flowmeter of claim 1, configured to provide a first measurement where the input electric signal has a first frequency, and a second measurement, where the input electric signal has a second frequency, wherein the first frequency is higher than the second frequency.

4. The electromagnetic flowmeter of claim 3, wherein signal processor is configured to determine, based on the first and second measurements, respectively, a dielectric constant and a conductivity of the fluid composition.

5. The electromagnetic flowmeter of claim 4, wherein the signal processor is configured to determine any of a water content, an oil content, a gas content, a water-in-oil-ratio, an oil-in-water ratio, and a gas in oil ratio of the fluid composition, based on the dielectric constant and the conductivity of the fluid composition.

6. The electromagnetic flowmeter of claim 1, wherein the signal processor is configured to detect voltages and a phase difference of signals input on the first and second ports of the first electric conductor.

7. The electromagnetic flowmeter of claim 1, wherein the first dual signal detector comprises a bidirectional bridge with dual RMS and Peak-to-Peak detectors and a phase detector.

8. A method for measuring a property of a fluid composition carried in a fluid conduit comprising the steps of:

inducing a Radio Frequency electromagnetic wave in the fluid conduit by supplying an input Radio Frequency electric signal to a first end of a first electric conductor inside the fluid conduit, where the electric conductor is part of a transmission line;

receiving an output Radio Frequency electric signal from a second end of the first electric conductor; and determining a property of the fluid composition based on the input Radio Frequency electric signal, the reflected signal on the first end, and the output Radio Frequency electric signal, wherein the first electric conductor is a metal wire configured to be arranged as a spiral inside the fluid conduit, and the spiral metal wire is embedded in an insulating liner.

9. The method of claim 8, wherein the input electric signal has an analog sinusoidal waveform.

10. The method of claim 8, wherein the step of determining the property further comprises comparing amplitude and phase of any of the input electric signal, the output electric signal and the reflected input electric signal.

11. The method of claim 8, further comprising providing a first measurement where the input electric signal has a first frequency, and a second measurement, where the input electric signal has a second frequency, wherein the first frequency is higher than the second frequency.

12. The method of claim 11, further comprising determining, based on the first and second measurements, respectively, a dielectric constant and a conductivity of the fluid composition.

13. The method of claim 12, further comprising determining any of a water content, an oil content, a gas content, a water-in-oil-ratio, an oil-in-water ratio, and a gas in oil ratio of the fluid composition, based on the dielectric constant and the conductivity.

* * * * *